(12) United States Patent
Duong et al.

(10) Patent No.: US 7,381,207 B2
(45) Date of Patent: *Jun. 3, 2008

(54) QUICK DISCONNECT ASSEMBLY HAVING A FINGER LOCK ASSEMBLY

(75) Inventors: Thach Duong, Tustin, CA (US); Jay J. Eum, Irvine, CA (US)

(73) Assignee: Endocare, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/685,058

(22) Filed: Mar. 12, 2007

(65) Prior Publication Data

US 2007/0167939 A1   Jul. 19, 2007

Related U.S. Application Data

(63) Continuation-in-part of application No. 11/116,873, filed on Apr. 28, 2005, now Pat. No. 7,189,228, and a continuation-in-part of application No. 10/603,883, filed on Jun. 25, 2003, now Pat. No. 7,207,985.

(51) Int. Cl.
*A61B 18/02*     (2006.01)

(52) U.S. Cl. .......................................... 606/20; 606/23

(58) Field of Classification Search ............ 606/20–31; 607/88–92; 403/280–287, 289–305
See application file for complete search history.

(56) References Cited

U.S. PATENT DOCUMENTS 3,524,446 A     8/1970   Crump et al.

(Continued)

*Primary Examiner*—Ahmed M Farah
(74) *Attorney, Agent, or Firm*—Lawrence N. Ginsberg

(57) ABSTRACT

The quick disconnect assembly includes a reusable assembly including a distal end having a male lip thereon; and, a disposable assembly having quick disconnect capabilities when utilized with the reusable assembly. The disposable assembly includes a stem section; a finger lock element; and, a detachable handle assembly. The finger lock element includes a distal finger lock element section having a threaded inner surface for engagement with a threaded outer surface of the stem section; and, a plurality of radially spaced fingers extending proximally from the distal finger lock element section. Each finger has a) a ramped surface for operatively engaging an associated ramp section on the stem section during use; and, b) a female lip at a proximal end thereof. The detachable handle assembly includes a proximal handle section having a distal end having an inner surface that is operatively engaged with an outer surface of the finger lock element so as to resist relative rotation and axial motion therebetween. A distal handle section of the detachable handle assembly includes a distal handle section having an inner surface that is operatively engaged with another outer surface of the stem section so as to resist relative rotation and axial motion therebetween. A breakaway collar of the detachable handle assembly is positioned between the proximal handle section and the distal handle section. When the disposable assembly is attached, the breakaway collar is an integral unit which prevents relative rotation between the proximal handle section and the distal handle section, the female lip engaging the male lip at a distal end of the reusable assembly, thereby securing the reusable assembly to the disposable assembly. The quick disconnect assembly may be used to provide only a mechanical connection or it may be provided with components for providing fluid transfer. In another embodiment, instead of only providing for single use, multiple use of a detachable assembly is provided by eliminating the breakaway collar and utilizing spring biasing means.

19 Claims, 6 Drawing Sheets

U.S. PATENT DOCUMENTS

| | | |
|---|---|---|
| 3,800,552 A | 4/1974 | Sollami |
| 4,018,227 A | 4/1977 | Wallach |
| 4,206,760 A | 6/1980 | Davis |
| 4,258,888 A | 3/1981 | Sawn |
| 5,224,943 A | 7/1993 | Goddard |
| 5,254,116 A | 10/1993 | Baust et al. |
| 5,452,582 A | 9/1995 | Longsworth |
| 5,520,682 A | 5/1996 | Baust et al. |
| 5,800,487 A | 9/1998 | Mikus |
| 5,910,104 A | 6/1999 | Dobak |
| 5,978,697 A | 11/1999 | Maytal |
| 5,992,158 A | 11/1999 | Goddard et al. |
| 6,039,730 A | 3/2000 | Rabin |
| 6,074,412 A | 6/2000 | Mikus |
| 6,106,517 A | 8/2000 | Zupkas |
| 6,306,129 B1 | 10/2001 | Little |
| 6,767,346 B2 | 7/2004 | Damasco |
| 7,160,291 B2 * | 1/2007 | Damasco et al. ............. 606/23 |
| 7,189,228 B2 * | 3/2007 | Eum et al. .................... 606/22 |
| 7,207,985 B2 * | 4/2007 | Duong et al. ................. 606/20 |
| 2002/0022832 A1 | 2/2002 | Mikus |
| 2002/0188287 A1 | 12/2002 | Zvuloni et al. |
| 2003/0055415 A1 | 3/2003 | Yu |
| 2003/0078570 A1 | 4/2003 | Heiner et al. |
| 2005/0010200 A1 | 1/2005 | Damasco |
| 2007/0191824 A1 * | 8/2007 | Duong et al. ................. 606/20 |

* cited by examiner

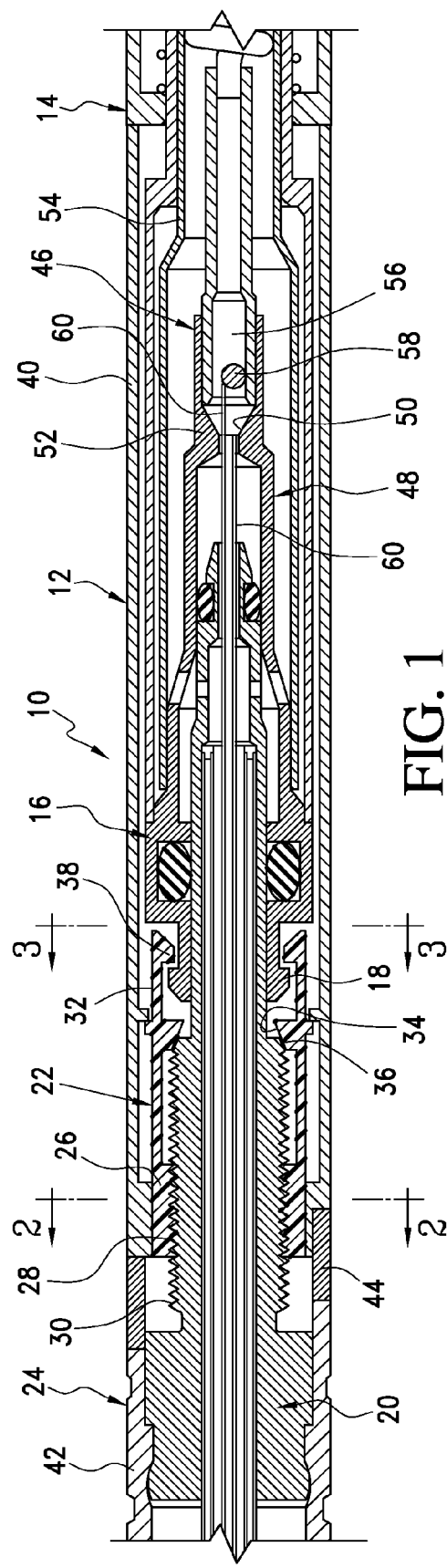

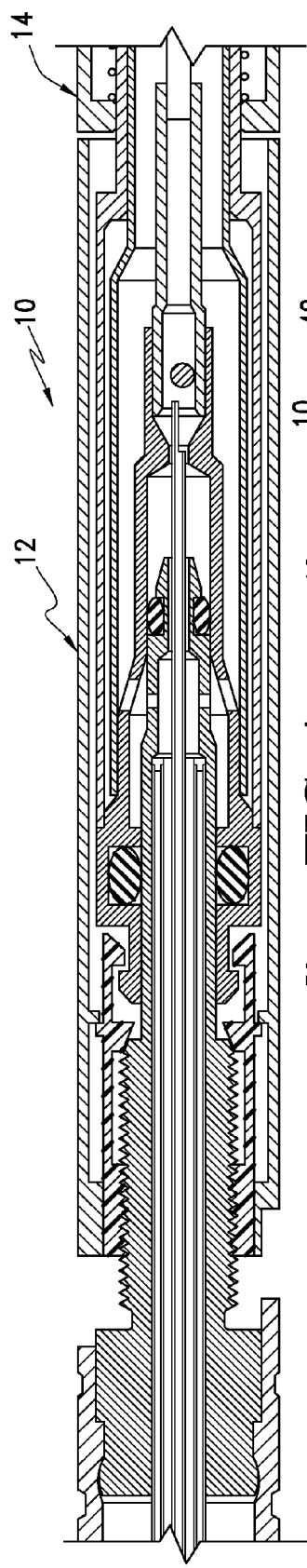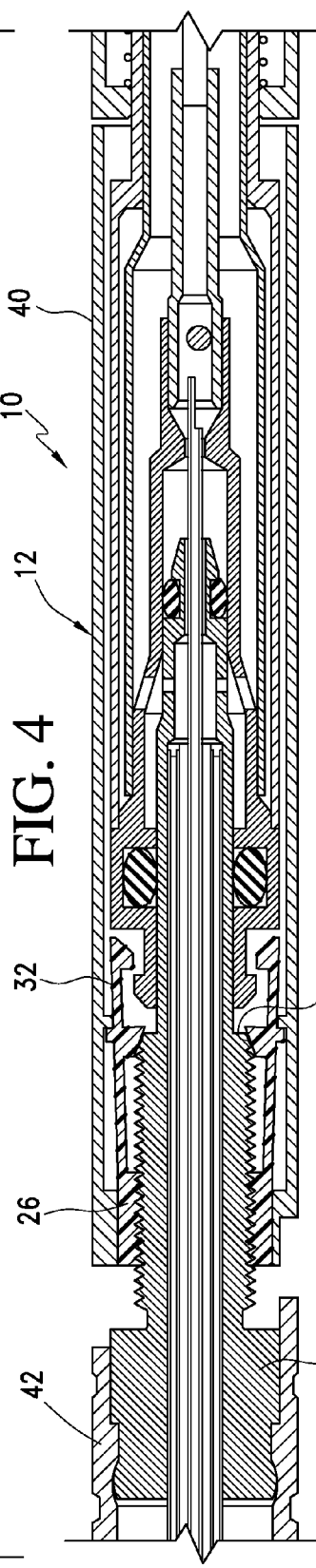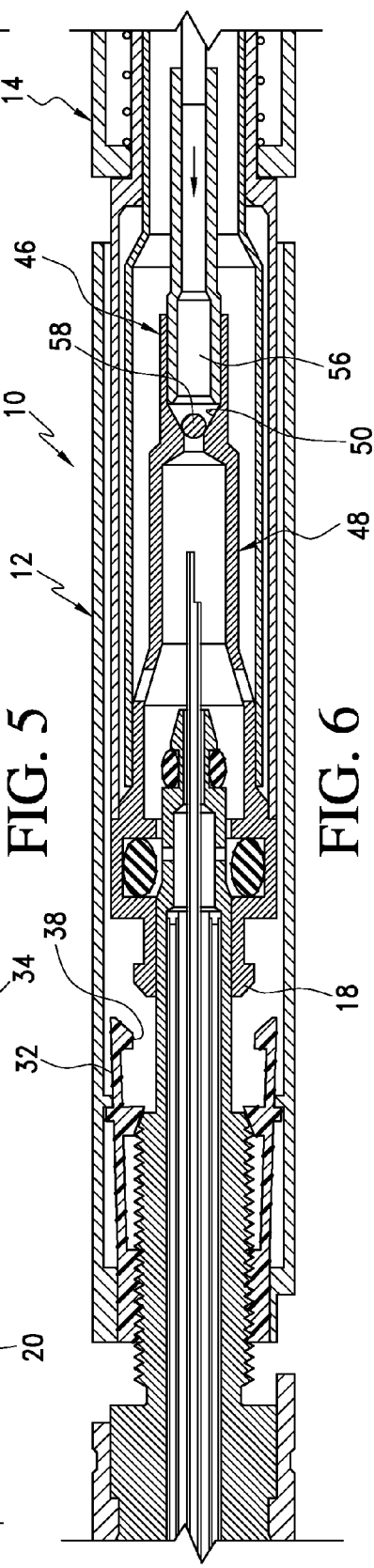

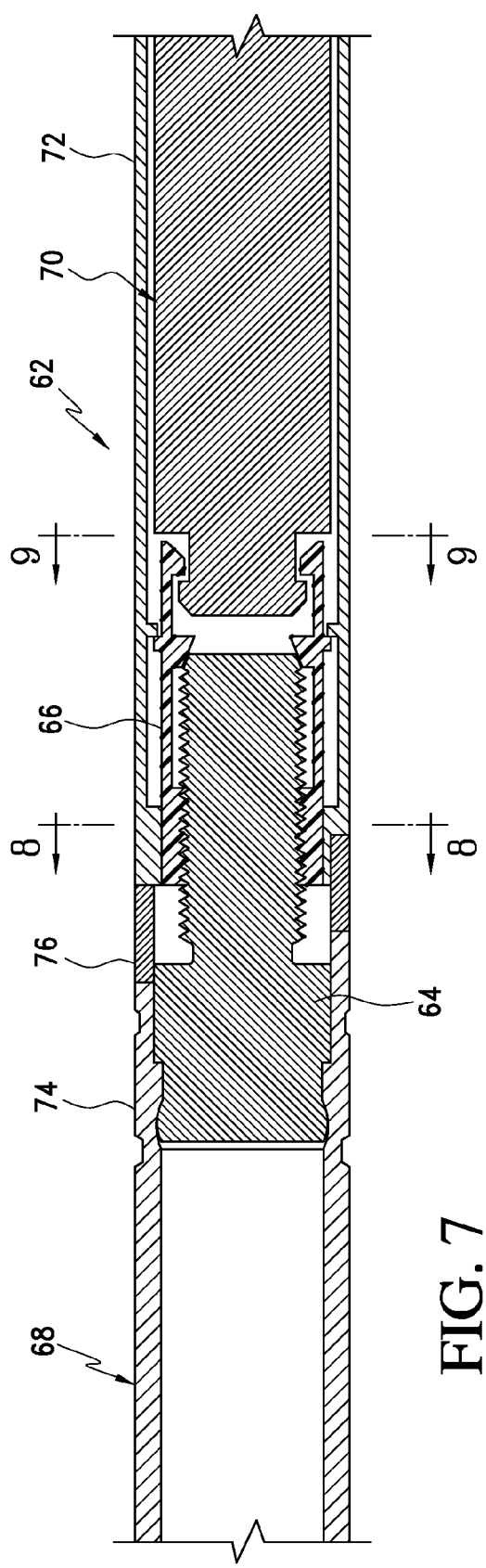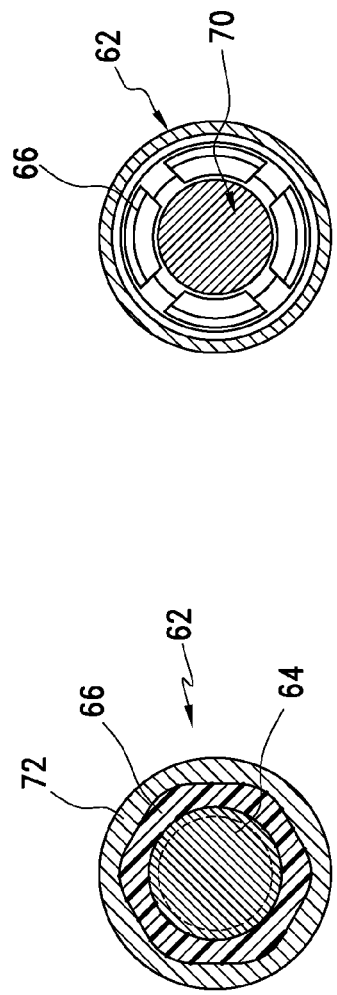

ated Apr. 28, 2005, which is a continuation-in-part
QUICK DISCONNECT ASSEMBLY HAVING A FINGER LOCK ASSEMBLY

CROSS REFERENCE TO RELATED APPLICATIONS

This is a continuation-in-part of U.S. Ser. No. 11/116,873, entitled Detachable Cryosurgical Probe With Breakaway Handle, filed Apr. 28, 2005, which is a continuation-in-part of U.S. Ser. No. 10/603,883, entitled Detachable Cryosurgical Probe, filed Jun. 25, 2003.

BACKGROUND OF THE INVENTION

1. Field of the Invention

The present invention relates to quick disconnect assemblies and more particularly to a quick disconnect assembly that utilizes a finger lock assembly for providing effective disconnect capabilities for both single and multiple uses; and, for with both purely mechanical systems and for systems that provide for fluid transfer.

2. Description of the Related Art

Cryosurgery involving the use of a cryosurgical probe assemblies typically involves the use of cryoprobes that are each attached to a handle that are, in turn, connected to a high-pressure fluid line with a quick-disconnect for attachment to a fluid source. There is an inherent problem with this type of system inasmuch as each cryosurgical probe assembly is typically used only once due to sterilization and performance factors. Therefore, typically, the entire cryosurgical probe assembly and high-pressure fluid line is often discarded after that single use. Due to these sterilization/performance requirements there is often a need to assure that the cryosurgical probe assembly may be rendered non-useable after a single-use.

Previous attempts to mitigate this problem have involved utilizing a disposable sheath over a cryosurgical probe. For example, U.S. Pat. No. 5,910,104, issued to J. D. Doback, III et al, discloses a disposable, sterilizable sheath for use on a closed loop Joule-Thomson cryosurgical probe, and the combination of the disposable sheath and the closed loop probe. The sheath is slipped over the probe, thereby separating the probe from the environment. The sheath has a grip that fits over the handle of the cryosurgical probe. The sheath has a hollow multi-lumen catheter shaped and sized to fit snugly over the cannula of the cryosurgical probe.

U.S. Pat. No. 6,306,129 B1, issued to Little et al, also discloses the use of a disposable sheath over a cryosurgical probe.

Similarly, U.S. Pat. Publication U.S. 2002/0022832 A1, to Mikus et al, discloses a cryoprobe assembly that includes a cryoprobe and an outer sheath assembly detachably connected thereto.

U.S. Pat. Publication U.S. 2004/0267248, to Duong et al, entitled "Detachable Cryosurgical Probe", discloses a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The cryosurgical probe system includes the capability of providing return fluid flow.

U.S. Pat. Publication U.S. 2005/0010200, to Damasco et al, entitled "Detachable Cryosurgical Probe", discloses a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The fluid connector assembly includes a substantially cylindrical lock housing securely attached to the outlet section of the fluid supply line, the lock housing having a fluid inlet conduit for receiving high pressure fluid from the fluid supply line and a fluid outlet conduit for transferring return fluid from the cryosurgical probe to the fluid supply line. A locking mechanism is positioned at a locking portion of the lock housing to provide detachable engagement of a cryosurgical probe positioned therein. The detachable cryosurgical probe receives fluid from the fluid connector assembly and manipulates the fluid to provide suitable temperatures for cryosurgical treatment. It includes a fluid delivery/return manifold assembly having a fluid delivery section and a return manifold section. The return manifold section is positioned over a portion of the fluid delivery section. The return manifold section includes an insulative vacuum sleeve. The fluid delivery/return manifold assembly has a proximal end section. An outer sheath is securely positioned over the vacuum sleeve and extends from the fluid delivery/return manifold assembly. A lock anchor is securely positioned over the outer sheath. The lock anchor provides detachable connection to the fluid connector assembly of a detachable cryosurgical system. During operation fluid is delivered through the fluid delivery/return manifold assembly, through a Joule-Thomson (J-T) port defined at a distal end of the fluid delivery section and is returned through the return manifold section and delivered out of the cryosurgical probe. The insulative vacuum sleeve is provided between the outer sheath and the return manifold section at a control region of the outer sheath proximal to a distally located treatment region of the outer sheath. Unlike previous cryosurgical probe systems, the operative portion of the present system, i.e. the detachable cryosurgical probe, can be discarded after a single use. However, the fluid supply line and the connector assembly can be reused. The cryosurgical probe system includes the capability of providing return fluid flow. Suitable passageways in the detachable cryosurgical probe and the fluid connector assembly provide this feature.

U.S. Pat. No. 5,978,697, issued to Maytal, et al, discloses an MRI-guided cryosurgical system. The Maytal system includes: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; and, (iii) a line member having a first end connectable to the operating member and a second end connectable to said control member, wherein at least a portion of the line member is received within the channel of the MRI magnet.

Although the need for most cryosurgical applications is for a detachable cryosurgical probe that is single use, there are also applications in which a multiple use probe is desired. Additionally, there is also, for many applications, a need to minimize the size of the quick disconnect assembly.

SUMMARY OF THE INVENTION

In a broad aspect, the present invention is embodied as a quick disconnect assembly, comprising: a reusable assembly including a distal end having a male lip thereon; and, a disposable assembly having quick disconnect capabilities when utilized with the reusable assembly. The disposable assembly includes a stem section; a finger lock element; and, a detachable handle assembly. The finger lock element includes a distal finger lock element section having a threaded inner surface for engagement with a threaded outer surface of the stem section; and, a plurality of radially spaced fingers extending proximally from the distal finger lock element section. Each finger has a) a ramped surface for operatively engaging an associated ramp section on the stem section during use; and, b) a female lip at a proximal end thereof. The detachable handle assembly includes a proximal handle section having a distal end having an inner surface that is operatively engaged with an outer surface of the finger lock element so as to resist relative rotation and axial motion therebetween. A distal handle section of the detachable handle assembly includes a distal handle section having an inner surface that is operatively engaged with another outer surface of the stem section so as to resist relative rotation and axial motion therebetween. A breakaway collar of the detachable handle assembly is positioned between the proximal handle section and the distal handle section. When the disposable assembly is attached, the breakaway collar is an integral unit which prevents relative rotation between the proximal handle section and the distal handle section, the female lip engaging the male lip at a distal end of the reusable assembly, thereby securing the reusable assembly to the disposable assembly. During an initial stage of detachment of the disposable assembly, the user rotates the proximal handle section in a first direction relative to the distal handle section to break away breakaway surfaces of the breakaway collar, allowing the breakaway collar to radially expand. During an intermediate stage of detachment of the disposable assembly the user counter rotates the distal handle section in an opposite second direction relative to the proximal handle section the relative rotation between the proximal handle section and the distal handle section providing axial movement of the distal handle section toward the proximal handle section via the engagement of the threaded inner surface of the distal finger lock element section and the threaded outer surface of the stem. The axial movement is enabled by the radial expansion of the breakaway collar, the ramped surfaces of the radially spaced fingers engaging the associated ramp section on the stem during the axial movement thereby urging the fingers to open. During a final stage of detachment the fingers open sufficiently to allow disengagement of the male lip from the female lip, thus enabling the disposable assembly to be detached from the reusable assembly.

The quick disconnect assembly may be used to provide only a mechanical connection or it may be provided with components for providing fluid transfer.

In another broad aspect, instead of only providing for single use, multiple use of a detachable assembly is provided by eliminating the breakaway collar and utilizing spring biasing means.

The present invention provides a unique capability of providing two simultaneous countercurrent flow paths. This benefit is particularly applicable for certain cryosurgical probe system applications in which there are simultaneous input and output flows. Furthermore, the finger lock element provides a minimized envelope.

BRIEF DESCRIPTION OF THE DRAWINGS

FIG. 1 is a cross-sectional view of a first embodiment of the quick disconnect assembly utilizing a disposable assembly shown in an attached configuration with a reusable assembly, this first embodiment providing fluid transfer.

FIG. 2 is a view taken along line 2-2 of FIG. 1.

FIG. 3 is a view taken along line 3-3 of FIG. 1.

FIG. 4 is a cross-sectional view of the quick disconnect assembly just after the breakaway collar has been detached.

FIG. 5 is a cross-sectional view of the quick disconnect assembly at the intermediate stage of detachment when the fingers are opening.

FIG. 6 is a cross-sectional view of the quick disconnect assembly at the final stage of detachment when the fingers have opened sufficiently to enable the disposable assembly to be detached from the reusable assembly.

FIG. 7 is a cross-sectional view of a second embodiment of the quick disconnect assembly utilizing a disposable assembly shown in an attached configuration with a reusable assembly, this second embodiment providing a mechanical connection without provision for fluid transfer.

FIG. 8 is a view taken along line 8-8 of FIG. 7.

FIG. 9 is a view taken along line 9-9 of FIG. 7.

The same elements or parts throughout the figures are designated by the same reference of characters.

DETAILED DESCRIPTION OF THE INVENTION

Figure 10:
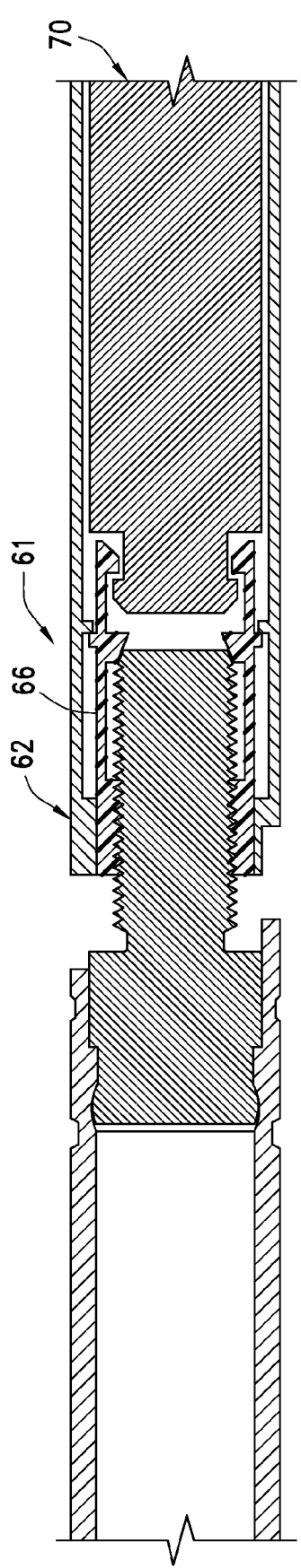
FIG. 10 is a cross-sectional view of the quick disconnect assembly of FIG. 7 just after the breakaway collar has been detached.

Referring now to the drawings and the characters of reference marked thereon, FIG. 1 illustrates a first embodiment of the quick disconnect assembly of the present invention, designated generally as 10. In this first embodiment the quick disconnect assembly includes a single use, disposable assembly 12 and a reusable assembly, designated generally as 14. In the parent application to this patent application the disposable assembly 12 and the reusable assembly 14 are explained in detail as applied in a cryosurgical probe system. The parent application, U.S. Ser. No.

11/116,873, entitled Detachable Cryosurgical Probe With Breakaway Handle, filed Apr. 28, 2005, is incorporated by reference herein, in its entirety. FIG. 1 of the present patent application shows the attaching portions of the disposable assembly 12 and the reusable assembly 14, as applied to this cryosurgical probe system. However, this disconnect assembly 10 can be used in numerous applications involving fluid transfer such as control valves for water heaters, pneumatic or hydraulic systems for controls, and intravenous systems.

The reusable assembly 14 has a distal end 16 with a male lip 18. The disposable assembly includes a stem section 20; a finger lock element 22, and a detachable handle assembly 24. The finger lock element 22 includes a distal finger lock element section 26 having a threaded inner surface 28 for engagement with a threaded outer surface 30 of the stem section 20. A plurality (i.e. four) radially spaced fingers 32 (see also FIG. 3) extend proximally from the distal finger lock element section 26. Each finger has a) a ramped surface 34 for operatively engaging an associated ramp section 36 on the stem section 20 during use; and, b) a female lip 38 at a proximal end thereof.

The detachable handle assembly 24 includes a proximal handle section 40 having a distal end having an inner surface that is operatively engaged with an outer surface of said finger lock element so as to resist relative rotation and axial motion therebetween. As can be seen in FIG. 2, hex shaped surfaces are utilized to prevent relative rotation; however, obviously other geometric shapes and other means can be used to prevent such rotation such as radial bumps, pins, etc.

A distal handle section 42 has an inner surface that is operatively engaged with another outer surface of the stem section so as to resist relative rotation and axial motion therebetween. Again, this region of engagement may be hex shaped. A breakaway collar 44 is positioned between the proximal handle section 40 and the distal handle section 42.

In operation, when the disposable probe assembly is attached, as can be seen in FIG. 1 the breakaway collar 44 is an integral unit that prevents relative rotation between the proximal handle section 40 and the distal handle section 42. In this configuration, the female lip 38 engages the male lip 18 of the reusable assembly; thereby securing the reusable assembly 14 to the disposable assembly 12.

During an initial stage of detachment of the disposable assembly 12, the user rotates the distal handle section in a first direction relative to the proximal handle section to "break away" breakaway surfaces of the breakaway collar 44, allowing the breakaway collar 44 to radially expand. In FIG. 4 the breakaway collar 44 is shown removed; however, during actual operation it may possibly dangle at that location.

Referring now to FIG. 5, during an intermediate stage of detachment of the disposable assembly 12 the user counter rotates the distal handle section 42 in an opposite second direction relative to the proximal handle section 40. The relative rotation between the distal handle section 42 and the proximal handle section 40 provides axial movement of the distal handle section 42 toward the proximal handle section 40 via the engagement of the threaded inner surface of the distal finger lock element section 26 and the threaded outer surface of the stem section 20. The axial movement is enabled by the radial expansion (and removal) of the breakaway collar 44. The ramped surfaces 34 of the radially spaced fingers 32 engage the associated ramp section on the stem section 20 during the axial movement thereby urging the fingers 32 to open.

Referring now to FIG. 6, during a final stage of detachment, the fingers 32 open sufficiently to allow disengagement of the male lip 18 from the female lip 38, thus enabling the disposable assembly 12 to be detached from the reusable assembly 14.

If the quick disconnect assembly 10 provides fluid transfer capablilites, such as in the cryosurgical probe system illustrated, the reusable assembly 14 preferably includes a safety valve assembly, designated generally as 46, operatively engaged with a manifold assembly 48 for impeding cryogenic working fluid flow when the disposable assembly 12 is detached from the reusable assembly 14. The safety valve assembly 46 includes a conical surface 50 formed in a proximal penultimate section 52 of a proximal end portion of the manifold assembly 48. The manifold assembly 48 terminates, at its proximate end, with a proximal ultimate section 54. The proximal ultimate section 54 has a ball retaining cavity 56 formed therein. A ball 58 is positioned within the ball retaining cavity 56.

As can be seen in FIG. 6, when the disposable assembly 12 is detached from the reusable probe assembly 14 and no cooling gas is flowing within manifold assembly 48, the ball 58 is free to float freely within the ball retaining cavity 56. However, when the disposable assembly 12 is detached from the reusable probe assembly 14 and cooling gas is flowing within the manifold assembly 48, the ball 58 is urged into a volume defined by the conical surface 50, thus providing sufficient sealing to prevent "whipping" of the disposable probe assembly 12. As perhaps best seen in FIG. 1, when the disposable assembly 12 is connected to the reusable probe assembly 14 the tube 60 bonded to the stem section 20 maintains the ball 58 in a position away from the conical surface 50, thus allowing the free flow of cooling gas into the disposable probe assembly 12. In the instance of present applicants' cryosurgical application this tube is a Joule-Thomson (J-T) tube. However, it is understood that for other applications the tube would generally be the fluid delivery tube for the fluid being transferred. Alternatively, another element associated with the stem section 20 can be operatively engageable with the ball 58 to provide this safety function.

Referring now to FIGS. 7-12, another embodiment of a quick disconnect assembly is illustrated, designated generally as 61 which utilizes a reusable assembly, designated generally as 62, that provides a mechanical connection without provision for fluid transfer. In such an instance the basic components are similar to those of the first embodiment; however, disposable assembly 62 provides a purely mechanical connection. Its components include a stem section 64; a finger lock element 66; and, a detachable handle assembly 68. The detachable handle assembly 62 attaches to a reusable assembly 70. The detachable handle assembly 68 includes a proximal handle section 72, a distal handle section 74; and, a breakaway collar 76 positioned between the proximal handle section 72 and the distal handle section 74.

Figure 11:
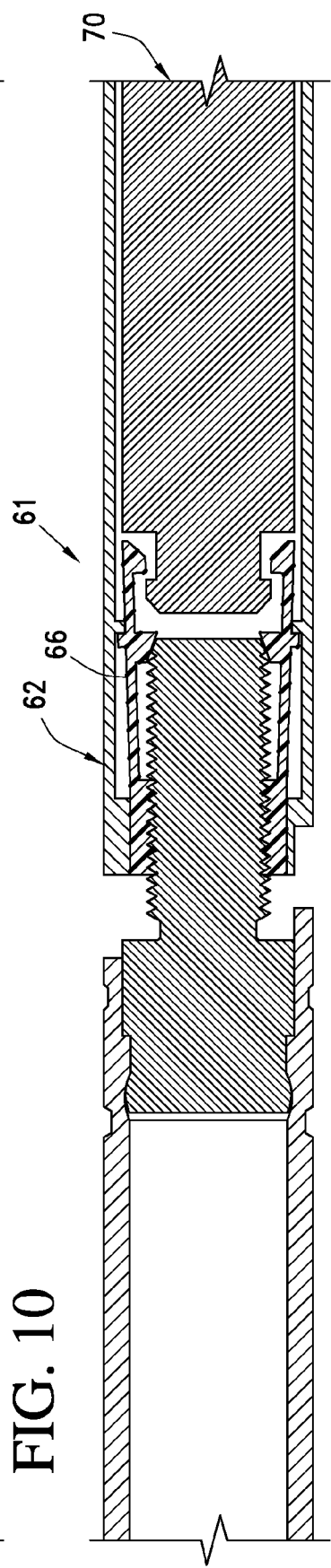
FIG. 11 is a cross-sectional view of the quick disconnect assembly of FIG. 7 at the intermediate stage of detachment when the fingers are opening.
Figure 12:
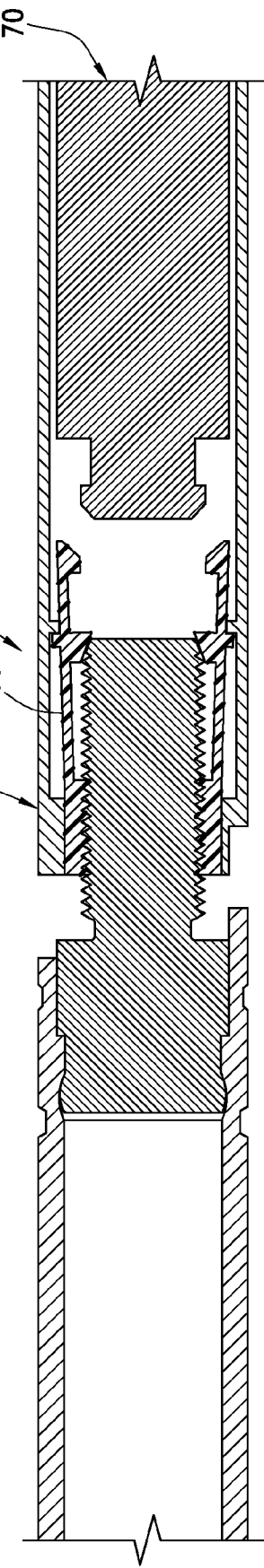
FIG. 12 is a cross-sectional view of the quick disconnect assembly of FIG. 7 at the final stage of detachment when the fingers have opened sufficiently to enable the disposable assembly to be detached from the reusable assembly.

FIGS. 10-12 sequentially illustrate the opening of the finger lock element 66 to allow detachment of the disposable assembly 62. This single use, mechanical version of the present invention may be used for a variety of purposes such as test fixtures, ropes, rods, etc.

Figure 13:
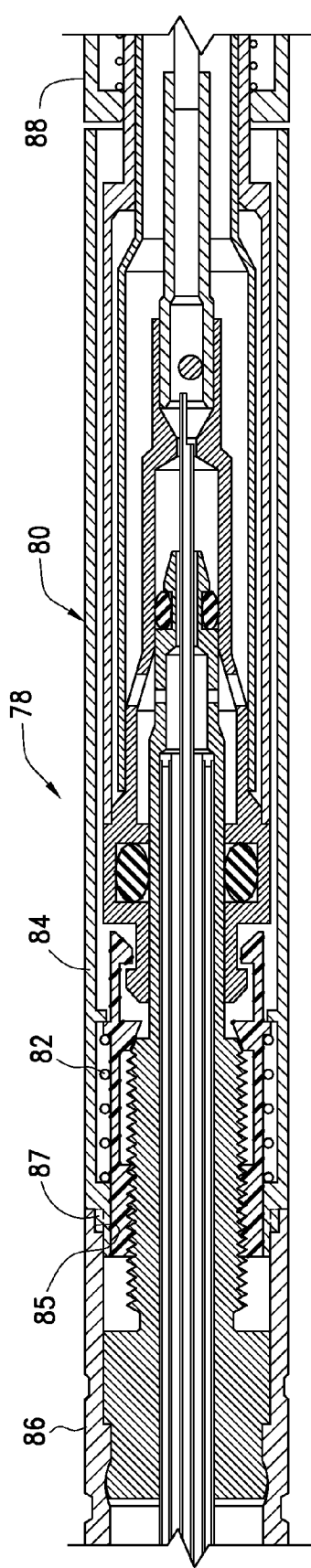
FIG. 13 is a cross-sectional view of a third embodiment of the quick disconnect assembly utilizing a detachable assembly allowing multiple use, the detachable assembly shown in an attached configuration with a connector assembly, this embodiment providing for fluid transfer.
Figure 14:
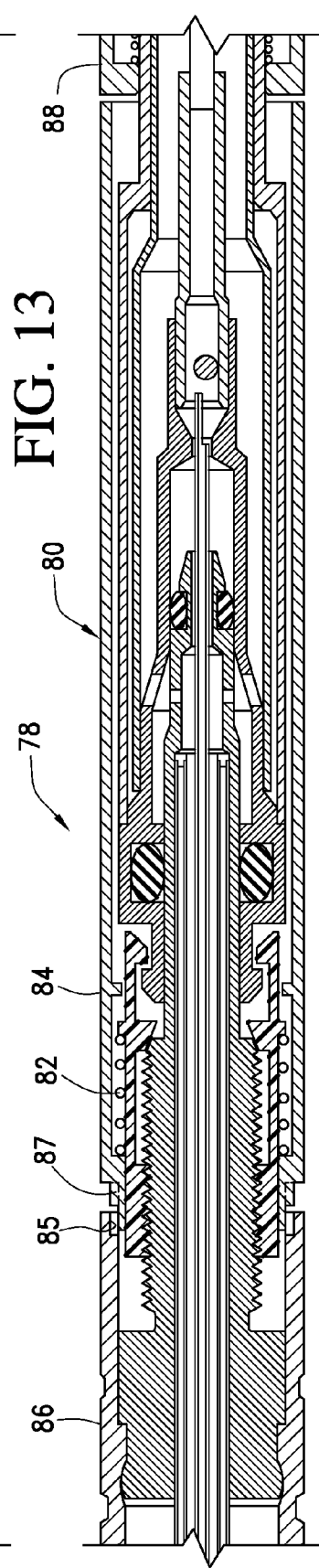
FIG. 14 is a cross-sectional view of the quick disconnect assembly of FIG. 13 at the intermediate stage of detachment when the fingers are opening.
Figure 15:
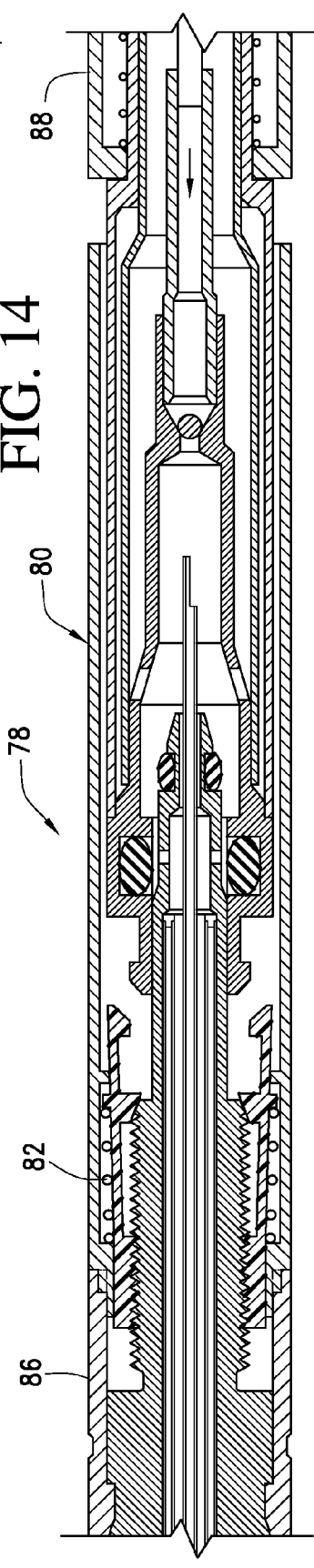
FIG. 15 is a cross-sectional view of the quick disconnect assembly of FIG. 13 at the final stage of detachment when the fingers have opened sufficiently to enable the detachable assembly to be detached from the connector assembly.

Referring now to FIGS. 13-15 another embodiment of the quick disconnect assembly is illustrated, designated generally as 78. This embodiment provides for multiple use of a detachable assembly 80. The breakaway collar of the first embodiment is eliminated and a spring 82 is utilized instead. The spring 82 is positioned within the proximal handle section 84 so as to bias a distal end of the proximal handle section 84 against a proximal end of the distal handle section 86 thereof. In FIG. 13, the distal handle section 86 cannot rotate relative to the proximal handle section 84 due to notches 85, 87. For disengagement, as shown in FIG. 14, the user pulls proximal handle section 84 away from distal handle section 86 creating a gap allowing the female notch 85 to disengage from male boss 87. The stem section can then advance along the ramp on the finger lock element. Ultimately, as shown in FIG. 15, disengagement of the detachable assembly 80 from a connector assembly 88 is provided.

Figure 16:
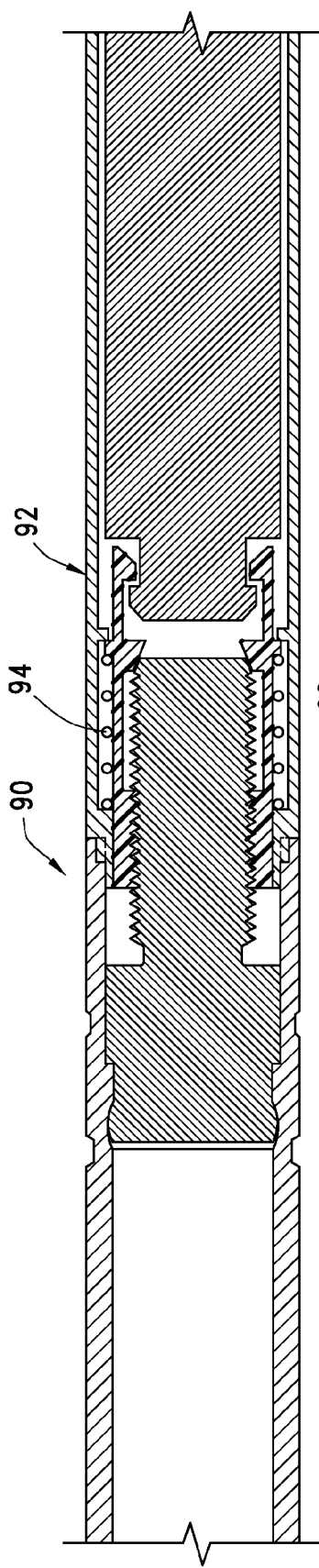
FIG. 16 is a cross-sectional view of another multiple use embodiment with the quick disconnect assembly in a fully attached configuration, this embodiment providing a mechanical connection without provision for fluid transfer.
Figure 17:
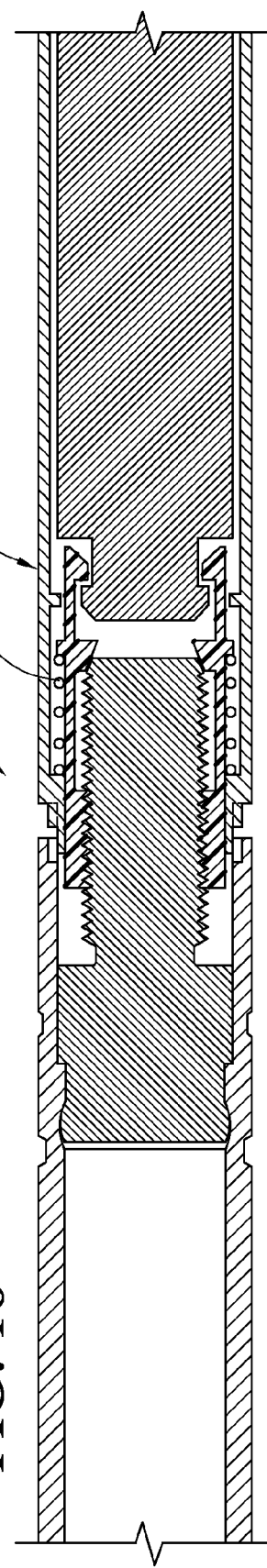
FIG. 17 is a cross-sectional view of the quick disconnect assembly of FIG. 16 at the intermediate stage of detachment when the fingers are opening.
Figure 18:
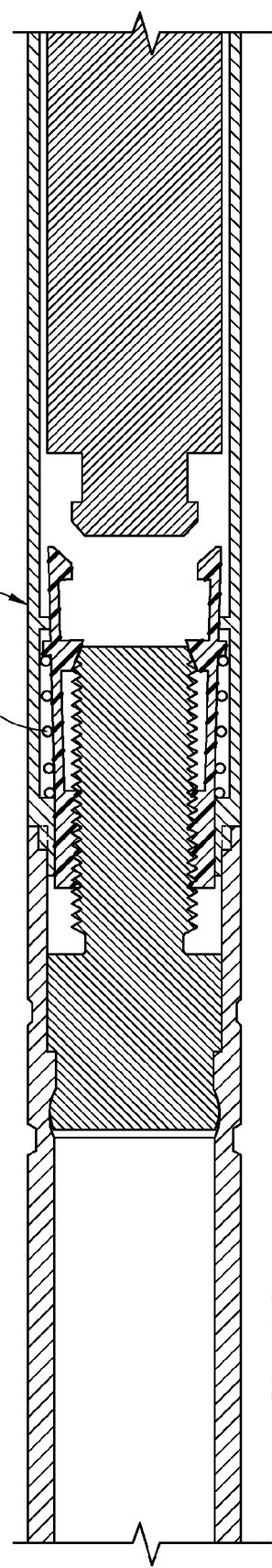
FIG. 18 is a cross-sectional view of the quick disconnect assembly of FIG. 16 at the final stage of detachment when the fingers have opened sufficiently to enable the detachable assembly to be detached from the connector assembly.

Referring now to FIGS. 16-18 another embodiment of the quick disconnect assembly is illustrated, designated generally as 90. This embodiment provides for multiple use of a detachable assembly 92; however with this embodiment there is no ability to provide fluid transfer. Instead, only a mechanical connection is provided. As in the FIG. 10-12 embodiment the components required for providing fluid transfer are eliminated. As in the FIG. 13-15 embodiment the requirement for a breakaway collar is eliminated and spring 94 is utilized. This embodiment operates in the same manner as described above relative to FIGS. 13-15.

Other embodiments and configurations may be devised without departing from the spirit of the invention and the scope of the appended claims.

The invention claimed is:

1. A disposable assembly having quick disconnect capabilities when utilized with a reusable assembly, comprising:
   a) a stem section;
   b) a finger lock element, comprising:
      i. a distal finger lock element section having a threaded inner surface for engagement with a threaded outer surface of said stem section; and,
      ii. a plurality of radially spaced fingers extending proximally from said distal finger lock element section, each finger having a) a ramped surface for operatively engaging an associated ramp section on said stem section during use; and, b) a female lip at a proximal end thereof; and
   c) a detachable handle assembly, comprising:
      i. a proximal handle section having a distal end having an inner surface that is operatively engaged with an outer surface of said finger lock element so as to resist relative rotation and axial motion therebetween;
      ii. a distal handle section having an inner surface that is operatively engaged with another outer surface of said stem section so as to resist relative rotation and axial motion therebetween; and,
      iii. a breakaway collar positioned between said proximal handle section and said distal handle section, wherein,
   1) when the disposable assembly is attached, said breakaway collar is an integral unit which prevents relative rotation between said proximal handle section and said distal handle section, said female lip engaging a male lip at a distal end of a reusable assembly, thereby securing the reusable assembly to said disposable assembly;
   2) during an initial stage of detachment of said disposable assembly, rotation of said proximal handle section in a first direction relative to said distal handle section breaks away breakaway surfaces of said breakaway collar, allowing said breakaway collar to radially expand;
   3) during an intermediate stage of detachment of said disposable assembly counter rotation of said distal handle section in an opposite second direction relative to said proximal handle section, the relative rotation between said proximal handle section and said distal handle section provides axial movement of said distal handle section toward said proximal handle section via said engagement of said threaded inner surface of said distal finger lock element section and said threaded outer surface of said stem section, said axial movement being enabled by said radial expansion of said breakaway collar, said ramped surfaces of said radially spaced fingers engaging said associated ramp section on said stem during said axial movement thereby urging said fingers to open; and,
   4) during a final stage of detachment said fingers open sufficiently to allow disengagement of the male lip from said female lip, thus enabling said disposable assembly to be detached from the reusable assembly.

2. The disposable assembly of claim 1, wherein said stem section comprises a fluid conduit subassembly.

3. The disposable assembly of claim 1, wherein said stem section comprises a fluid conduit subassembly for delivering and returning cooling fluid used for cryogenic cooling.

4. The disposable assembly of claim 1, wherein said stem section, said finger lock element and said detachable handle assembly comprise components of a detachable cryosurgical probe.

5. The disposable assembly of claim 1, wherein said stem section, said finger lock element and said detachable handle assembly comprise components of a control valve for a water heater.

6. The disposable assembly of claim 1, wherein said stem section, said finger lock element and said detachable handle assembly comprise components of a pneumatic system.

7. The disposable assembly of claim 1, wherein said stem section, said finger lock element and said detachable handle assembly comprise components of an electrical system.

8. A finger lock assembly for a disposable assembly normally attached to a reusable assembly, said disposable assembly being of a type having a handle assembly including: 1) a proximal handle section, 2) a distal handle section, and 3) a breakaway collar positioned between said proximal handle section and said distal handle section, said finger lock assembly, comprising:
   a finger lock element, comprising:
      i. a distal finger lock element section having a threaded inner surface for engagement with a threaded outer surface of a stem section of said disposable assembly; and,
      ii. a plurality of radially spaced fingers extending proximally from said distal finger lock element section, each finger having a) a ramped surface for operatively engaging an associated ramp section on said disposable assembly during use; and, b) a female lip at a proximal end thereof, wherein,
   1) when the disposable assembly is attached, said breakaway collar is an integral unit which prevents relative rotation between said proximal handle section and said distal handle section, said female lip engaging said male lip, thereby securing said reusable assembly to said disposable assembly;
   2) during an initial stage of detachment of said disposable probe assembly, rotation of said distal handle section in a first direction relative to said proximal handle section breaks away breakaway surfaces of said breakaway collar, allowing said breakaway collar to radially expand;
   3) during an intermediate stage of detachment of said disposable assembly counter rotation of said distal handle section in an opposite second direction relative to said proximal handle section, the relative rotation between said proximal handle section and said distal handle section provides axial movement of said distal handle section toward said proximal handle section via said engagement of said threaded inner surface of said distal finger lock element section and said threaded outer surface of said stem section, said axial movement being enabled by said radial expansion of said breakaway collar, said ramped surfaces of said radially spaced fingers engaging said associated ramp section on said stem section during said axial movement thereby urging said fingers to open; and, 4) during a final stage of detachment said fingers open sufficiently to allow disengagement of said male lip from said female lip, thus enabling said disposable probe assembly to be detached from said reusable probe assembly.

9. A quick disconnect assembly, comprising:
a) a reusable assembly including a distal end having a male lip thereon;
b) disposable assembly having quick disconnect capabilities when utilized with said reusable assembly, comprising:
   i. a stem section;
   ii. a finger lock element, comprising:
      1. a distal finger lock element section having a threaded inner surface for engagement with a threaded outer surface of said stem section; and,
      2. a plurality of radially spaced fingers extending proximally from said distal finger lock element section, each finger having a) a ramped surface for operatively engaging an associated ramp section on said stem section during use; and, b) a female lip at a proximal end thereof; and
   iii. a detachable handle assembly, comprising:
      1. a proximal handle section having a distal end having an inner surface that is operatively engaged with an outer surface of said finger lock element so as to resist relative rotation and axial motion therebetween;
      2. a distal handle section having an inner surface that is operatively engaged with another outer surface of said stem section so as to resist relative rotation and axial motion therebetween; and,
      3. a breakaway collar positioned between said proximal handle section and said distal handle section, wherein,
1) when the disposable assembly is attached, said breakaway collar is an integral unit which prevents relative rotation between said proximal handle section and said distal handle section, said female lip engaging said male lip at a distal end of said reusable assembly, thereby securing the reusable assembly to said disposable assembly;
2) during an initial stage of detachment of said disposable assembly, rotation of said proximal handle section in a first direction relative to said distal handle section breaks away breakaway surfaces of said breakaway collar, allowing said breakaway collar to radially expand;
3) during an intermediate stage of detachment of said disposable assembly counter rotation of said distal handle section in an opposite second direction relative to said proximal handle section, the relative rotation between said proximal handle section and said distal handle section provides axial movement of said distal handle section toward said proximal handle section via said engagement of said threaded inner surface of said distal finger lock element section and said threaded outer surface of said stem, said axial movement being enabled by said radial expansion of said breakaway collar, said ramped surfaces of said radially spaced fingers engaging said associated ramp section on said stem during said axial movement thereby urging said fingers to open; and,
4) during a final stage of detachment said fingers open sufficiently to allow disengagement of said male lip from said female lip, thus enabling said disposable assembly to be detached from said reusable assembly.

10. The quick disconnect assembly of claim 1, wherein said reusable assembly further comprises a safety valve assembly operatively engaged with a manifold assembly of the disposable assembly for impeding working fluid flow when the disposable assembly is detached from a reusable assembly, said safety valve assembly, comprising:
a) a conical surface formed in a proximal penultimate section of a proximal end portion of a manifold assembly of the disposable assembly, said manifold assembly terminating at its proximate end with a proximal ultimate section, said proximal ultimate section having a ball retaining cavity formed therein; and,
b) a ball positioned within said ball retaining cavity, wherein,
   1) when said disposable assembly is detached from said reusable assembly and no cooling gas is flowing within said manifold assembly, said ball is free to float freely within said ball retaining cavity;
   2) when said disposable assembly is detached from said reusable assembly and cooling gas is flowing within said manifold assembly, said ball is urged into a volume defined by said conical surface, thus providing sufficient sealing to prevent "whipping" of said disposable probe assembly; and,
   3) when said disposable probe assembly is connected to said reusable probe assembly a fluid delivery tube bonded to said stem section maintains said ball in a position away from said conical surface, thus allowing the free flow of cooling gas into said disposable assembly.

11. A detachable assembly having quick disconnect capabilities when utilized with a connector assembly, comprising:
a) a stem section;
b) a finger lock element, comprising:
   i. a distal finger lock element section having a threaded inner surface for engagement with a threaded outer surface of said stem section; and,
   ii. a plurality of radially spaced fingers extending proximally from said distal finger lock element section, each finger having a) a ramped surface for operatively engaging an associated ramp section on said stem section during use; and, b) a female lip at a proximal end thereof; and
c) a detachable handle assembly, comprising:
   i. a proximal handle section having a distal end having an inner surface that is operatively engaged with an outer surface of said finger lock element so as to resist relative rotation and axial motion therebetween;
   ii. a distal handle section having an inner surface that is operatively engaged with another outer surface of said stem section so as to resist relative rotation and axial motion therebetween; and, iii. a spring positioned within said proximal handle section so as to bias a distal end of said proximal handle section against a proximal end of said distal handle section, wherein, 1) when the detachable assembly is attached to said connector assembly, said female lip engages a male lip at a distal end of a connector assembly, thereby securing the quick disconnect assembly to said connector assembly;
3) during an initial stage of detachment of said detachable assembly rotation of said distal handle section relative to said proximal handle section, the relative rotation between said proximal handle section and said distal handle section providing axial movement of said finger lock element along said stem in a distal direction via said engagement of said threaded inner surface of said distal finger lock element section and said threaded outer surface of said stem, said ramped surfaces of said radially spaced fingers engaging said associated ramp section on said stem during said axial movement thereby urging said fingers to open; and,
4) during a final stage of detachment said fingers open sufficiently to allow disengagement of the male lip from said female lip, thus enabling the detachable assembly to be detached from the connector assembly.

12. The detachable assembly of claim 11, wherein said stem section comprises a fluid conduit subassembly.

13. The detachable assembly of claim 11, wherein said stem section comprises a fluid conduit subassembly for delivering and returning cooling fluid used for cryogenic cooling.

14. The detachable assembly of claim 11, wherein said stem section, said finger lock element and said detachable handle assembly comprise components of a detachable cryosurgical probe.

15. The detachable assembly of claim 11, wherein said stem section, said finger lock element and said detachable handle assembly comprise components of a control valve for a water heater.

16. The detachable assembly of claim 11, wherein said stem section, said finger lock element and said detachable handle assembly comprise components of a pneumatic system.

17. The detachable assembly of claim 11, wherein said stem section, said finger lock element and said detachable handle assembly comprise components of an electrical system.

18. A finger lock assembly for a detachable cryosurgical probe of a type including a disposable probe assembly normally attached to a reusable probe assembly, said disposable handle assembly including: 1) a proximal handle section, 2) a distal handle section, and 3) a breakaway collar positioned between said proximal handle section and said distal handle section, said locking assembly, comprising:

a finger lock element, comprising:
i. a distal finger lock element section having a threaded inner surface for engagement with a threaded outer surface of a gas delivery assembly of the disposable probe assembly; and,
ii. a plurality of radially spaced fingers extending proximally from said distal finger lock element section, each finger having a) a ramped surface for operatively engaging an associated ramp section on said gas delivery assembly during use; and, b) a female lip at a proximal end thereof, wherein, 1) when the disposable probe assembly is attached, said breakaway collar is an integral unit which prevents relative rotation between said proximal handle section and said distal handle section, said female lip engaging said male lip, thereby securing said reusable probe assembly to said disposable probe assembly;
2) during an initial stage of detachment of said disposable probe assembly, rotation of said distal handle section in a first direction relative to said proximal handle section breaks away breakaway surfaces of said breakaway collar, allowing said breakaway collar to radially expand;
3) during an intermediate stage of detachment of said disposable probe assembly counter rotation of said distal handle section in an opposite second direction relative to said proximal handle section, the relative rotation between said proximal handle section and said distal handle section provides axial movement of said distal handle section toward said proximal handle section via said engagement of said threaded inner surface of said distal finger lock element section and said threaded outer surface of said gas delivery assembly, said axial movement being enabled by said radial expansion of said breakaway collar, said ramped surfaces of said radially spaced fingers engaging said associated ramp section on said stem during said axial movement thereby urging said fingers to open; and,
4) during a final stage of detachment said fingers open sufficiently to allow disengagement of said male lip from said female lip, thus enabling said disposable probe assembly to be detached from said reusable probe assembly.

19. A safety valve assembly for a detachable cryosurgical probe of a type including a disposable probe assembly normally attached to a reusable probe assembly, comprising:

a) a conical surface formed in a proximal penultimate section of a proximal end portion of a manifold assembly of said reusable probe assembly for providing a flow of cooling gas, said manifold assembly terminating at its proximate end with a proximal ultimate section, said proximal ultimate section having a ball retaining cavity formed therein; and,
b) a ball positioned within said ball retaining cavity, wherein,
1) when said disposable probe assembly is detached from said reusable probe assembly and no cooling gas is flowing within said manifold assembly, said ball is free to float freely within said ball retaining cavity;
2) when said disposable probe assembly is detached from said reusable probe assembly and cooling gas is flowing within said manifold assembly, said ball is urged into a volume defined by said conical surface, thus providing sufficient sealing to prevent "whipping" of said disposable probe assembly; and,
3) when said disposable probe assembly is connected to said reusable probe assembly a Joule-Thomson (J-T) tube bonded to a gas delivery assembly of said disposable probe assembly maintains said ball in a position away from said conical surface, thus allowing the free flow of cooling gas into said disposable probe assembly.

* * * * *